United States Patent
Martin et al.

(10) Patent No.: US 8,334,271 B2
(45) Date of Patent: Dec. 18, 2012

(54) USE OF VEGF IN THE TREATMENT OF RETARDED FETAL GROWTH IN PREGNANCY

(75) Inventors: John Francis Martin, London (GB); Charles Henry Rodeck, London (GB)

(73) Assignee: Ark Therapeutics, Ltd., London (GB)

( * ) Notice: Subject to any disclaimer, the term of this patent is extended or adjusted under 35 U.S.C. 154(b) by 239 days.

(21) Appl. No.: 12/522,640

(22) PCT Filed: Feb. 22, 2008

(86) PCT No.: PCT/GB2008/000613
§ 371 (c)(1),
(2), (4) Date: Sep. 11, 2009

(87) PCT Pub. No.: WO2008/104747
PCT Pub. Date: Sep. 4, 2008

(65) Prior Publication Data
US 2010/0249015 A1    Sep. 30, 2010

(30) Foreign Application Priority Data
Feb. 26, 2007   (GB) .................................. 0703683.3

(51) Int. Cl.
*A61K 48/00* (2006.01)
*C07H 21/04* (2006.01)
*C12N 15/00* (2006.01)

(52) U.S. Cl. ....................... 514/44 R; 536/23.1; 435/455

(58) Field of Classification Search .................. 514/44 R
See application file for complete search history.

(56) References Cited

U.S. PATENT DOCUMENTS
7,030,083 B2   4/2006   Schreiner et al.
2004/0126828 A1   7/2004   Karumanchi et al.

FOREIGN PATENT DOCUMENTS
WO   WO 2006/034507 A   3/2006

OTHER PUBLICATIONS

Vandenbosche et al (American Family Physician, Oct. 15, 1998, p. 1-8.*
Simmons 2001, Diabetes, 50:2279-2286.*
Abstracts-Friday, *Journal of the Society for Gynecologic Investigation*, Feb. 2006, pp. 228A, vol. 13, No. 2.
Barry et al., "The pregnant sheep as a model for human pregnancy," *Theriogenology*, Nov. 5, 2007, pp. 55-67, vol. 69, No. 1.
Boulanger et al., "Avancees recentes dans la comprehension de la physiopathologie de la preeclampsia et consequences thereapeutiques potentielles," *Nephrologie & Therapeutique*, Nov. 26, 2007, pp. 437-448, vol. 3, No. 7, English Abstract.
Brownbill, P., et al., "Vasoactive and permeability effects of vascular endothelial growth factor-165 in the term in vitro dually perfused human placental lobule," *Endocrinology*, Oct. 2007, pp. 4734-4744, vol. 148, No. 10.
Karkkainen, Marika J., et al., "Vascular endothelial growth factor receptors in the regulation of angiogenesis and lymphangiogenesis," *Oncogene*, Nov. 20, 2000, pp. 5598-5608, vol. 19, No. 49.
Maynard, Sharon E., et al., "Excess placental soluble fms-like tyrosine kinase 1 (sFlt1) may contribute to endothelial dysfunction hypertension, and proteinuria in preeclampsia" *Journal of Clinical Investigation*, Mar. 2003, pp. 649-658, vol. 111, No. 5.
Szukiewicz, Dariusz et al., "Isolated placental vessel response to vascular endothelial growth factor and placenta growth factor in normal and growth-restricted pregnancy" *Gynecologic and Obstetric Investigation*, Dec. 9, 2004, pp. 102-107, vol. 59, No. 2.

\* cited by examiner

*Primary Examiner* — Valarie Bertoglio
(74) *Attorney, Agent, or Firm* — Pharmaceutical Patent Attorneys, LLC

(57) ABSTRACT

An agonist of the VEGF receptor is useful in the treatment of a disease associated with retarded fetal growth, such as intrauterine growth retardation. The VEGF agonist may be a VEGF peptide or a gene construct encoding or expressing such a peptide.

3 Claims, No Drawings

USE OF VEGF IN THE TREATMENT OF RETARDED FETAL GROWTH IN PREGNANCY

This application is a National Stage Application of International Application Number PCT/GB2008/000613, filed Feb. 22, 2008; which claims priority to United Kingdom Application No. 0703683.3, filed Feb. 26, 2007, which are incorporated herein by reference in their entirety.

FIELD OF THE INVENTION

This invention relates to the treatment of a disease associated with retarded fetal growth in pregnancy.

BACKGROUND OF THE INVENTION

Pregnancy is associated with an enormous increase in uterine perfusion, which results from increased maternal cardiac output and trophoblast-driven modification of the uterine spiral arteries. Failure of this normal physiological process is implicated in the aetiology of two of the most challenging obstetric complications, pre-eclampsia (PET) and fetal growth restriction (FGR), also called intra-uterine growth retardation (IUGR).

FGR affects up to 8% of all pregnancies, and is associated with a high perinatal mortality rate, long-term neurological impairment and an increased incidence of cardiovascular disease in later life; there is no effective evidence-based treatment. Severe early onset FGR affects 1:500 pregnancies, and is associated with high mortality and long term complications in survivors. An affected fetus may never achieve a viable delivery weight (at least 500 g) and the parents face a stark choice between termination of pregnancy, or allowing the fetus to die in utero. Small improvements in fetal growth (e.g. to a birthweight of 700 g) and in gestation at birth (e.g. from 26 to 28 weeks) are associated with major improvements in survival and morbidity.

Current antenatal care is designed to detect women who have growth restricted fetuses. A number of strategies such as maternal serum markers and uterine artery Doppler ultrasound examination are available, which may be able to predict the likelihood of the woman developing these conditions. However, there are currently no therapeutic strategies that will successfully prevent the development of FGR.

SUMMARY OF THE INVENTION

The present invention is based on a study (see below) that demonstrates for the first time in an in vivo animal model, that adenovirus-mediated local overexpression of VEGF results in increased uterine blood flow and relaxation of the uterine arteries. Low VEGF levels and reduced uterine blood flow are implicated in the aetiology of FGR. These results suggest therapeutic utility by increasing VEGF expression, to improve the outcome of pregnancies complicated by severe FGR.

According to the present invention, an agonist of the VEGF receptor is useful for the treatment of a disease associated with retarded fetal growth in pregnancy.

Active agents and vehicles that can be used in the invention are described in WO098/20027.

DESCRIPTION OF PREFERRED EMBODIMENTS

As used herein, a VEGF agonist is a molecule, which binds to a receptor to which VEGF binds. In particular, an agonist may bind to the flk-1/KDR or flt-1 receptors.

A VEGF agonist may have any chemical structure. For example, a VEGF agonist may be peptide or polypeptide of, for example, up to 10, up to 20, up to 50 or up to 100 amino acids. An agonist may similarly be a modified peptide, or a peptoid. Any suitable modification may be made, including glycosylation, sulphation, COOH-amidation and acetylation, e.g. N-terminal acetylation. Additionally, or alternatively, modified amino acids and/or L-amino acids may be present.

Alternatively, non-peptide VEGF agonists can be used. For example, small molecules that mimic the shape of the parts of VEGF that interact with its receptors may be used.

VEGF proteins for use in the invention that differ in sequence from naturally-occurring VEGF may be engineered to differ in activity from naturally-occurring VEGF. For example, they may be engineered to have stronger VEGF activity. Such manipulations will typically be carried out at the nucleic acid level using recombinant techniques known in the art.

In a preferred embodiment, the VEGF agonist is a VEGF peptide, or a gene construct encoding or expressing a VEGF peptide. In a more preferred embodiment, the VEGF peptide is VEGF-A or VEGF-D.

In practice of the invention, a VEGF peptide, a gene construct encoding such a peptide, a VEGF agonist or a nucleic acid encoding a VEGF agonist may be delivered to a blood vessel, preferably an artery, in any suitable form. Preferably, the VEGF agonist is administered to the uterine artery. Nucleic acids may be delivered in a "naked" form unassociated with a vector, or by means of a gene therapy vector. In particular, a viral or non-viral vector may be used.

Vectors, especially viral vectors, may be used in the invention, to achieve integration of the nucleic acid or construct into the genome of the cells of the subject to be treated, or to leave the nucleic acid or construct free in the cytoplasm. Integrative vectors are preferred.

A gene construct for use in the invention may be incorporated into a non-viral vector or viral genome by any suitable means known in the art. A viral genome may then be packaged into a viral coat or capsid by any suitable procedure. In particular, any suitable packaging cell line may be used to generate viral vectors of the invention. These packaging lines complement the replication-deficient viral genomes of the invention, as they include, typically incorporated into their genomes, the genes which have been deleted from the replication-deficient genome. Thus, the use of packaging lines allows viral vectors of the invention to be generated in culture. Suitable packaging lines include derivatives of PA317 cells, ψ-2 cells, CRE cells, CRIP cells, E-86-GP cells, Fly cells, line 293 cells and 293GP cells.

VEGF agonists of the invention may be administered by any form of administration, for example topical, cutaneous, parenteral, intramuscular, subcutaneous or transdermal administration, or by direct injection into the bloodstream, direct injection into or around the arterial wall or by direct application to mucosal tissues. Preferably, administration is by means of injections into the uterine artery.

The VEGF agonist may be delivered by means of an implant placed externally to a blood vessel, e.g. the uterine artery. Such an implant contains the VEGF agonist and provides a reservoir of the agent.

The VEGF agonist is preferably delivered in the form of a pharmaceutical formulation comprising a pharmaceutically acceptable carrier. Any suitable pharmaceutical formulation may be used.

For example, suitable formulations may include aqueous and non-aqueous sterile injection solutions which may contain anti-oxidants, buffers, bacteriostats, bactericidal antibiotics and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a frozen or freeze-dried (lyophilized) condition requiring only the addition of the sterile liquid carrier, for example water for injection, immediately prior to use.

It should be understood that, in addition to the ingredients particularly mentioned above, formulations of this invention may include other agents conventional in the art having regard to the type of formulation in question. Of the possible formulations, sterile pyrogen-free aqueous and non-aqueous solutions are preferred.

The VEGF agonist may be delivered in any suitable dosage, and using any suitable dosage regime. Those of skill in the art will appreciate that the dosage amount and regime may be adapted to ensure optimal treatment of the particular condition to be treated, depending on numerous factors. Some such factors may be the age, sex and clinical condition of the subject to be treated.

The dosage used for the delivery of a VEGF gene construct by means of a viral or non-viral vector will depend on many factors, including the efficiency with which the vectors deliver VEGF nucleic acids to cells, and the efficiency with which the VEGF nucleic acids are expressed in the cells. Dosage schedules will also vary according to, for example, the route of administration, the species of the recipient and the condition of the recipient. However, single doses and multiple doses spread over periods of days, weeks or months are envisaged.

Study
Materials and Methods
Experimental Animals:

Six Romney breed ewes that were pregnant with singleton (n=3) or twin (n=3) fetuses between 88 and 102 days of gestation (term 145 days of gestation) were used for these experiments. Ewes were time-mated after receiving intravaginal progesterone suppositories (manufacturer) for 2 weeks to induce ovulation. After with-holding of feed overnight, general anaesthesia was induced in the ewes with thiopentone IV (20 mg/kg manufacturer). The ewes were intubated with a size 11 endotracheal tube (Jorgen Kruuse, Denmark) and maintained on halothane 2% in $O_2$ via a Manley MP5 ventilator (Blease Medical Equipment Ltd, UK). Maternal pulse and respiratory rate, blood pressure, oxygen and carbon dioxide saturation and core temperature were measured throughout the procedure. Ewes received 01 mg/kg IM buprenorphine (Alstoe Animal Health, UK) for analgesia and Penstrep (procaine penicillin 200 mg/ml and dihydrostreptomycin sulphate 250 mg/ml, Norbrook Laboratories Ltd, UK) to prevent infection. The ewes recovered after extubation. The day following surgery fetal survival and wellbeing was monitored using ultrasound in all animals. All procedures on animals were conducted in accordance with UK Home Office regulations and the Guidance for the Operation of Animals (Scientific Procedures) Act (1986).

Ultrasound Examination of the Ewe and Fetus:

An Acuson 128 XP10 ultrasound scanner (Siemens, Bracknell, UK) was used for all ultrasound imaging. Fetal biometry was assessed before surgery and used to confirm the correct gestational age according to standard measurements (Barbera A, Jones O W et al., 1995; Kelly R W & Newnham J P, 1989; Kelly R W & Newnham J P, 1989). The ewe was ventilated for 30 minutes to achieve a steady state in the maternal oxygen and carbon dioxide levels, pulse and respiratory rate and temperature. The blood flow in the uterine arteries was assessed by color Doppler measurement using an Acuson C3 3.5 MHz curvilinear transducer. The external iliac artery was identified as it flowed in the maternal groin to the lower limb. The uterine artery (UtA) was identified just as it crossed over the external iliac artery and a Doppler waveform with at least 3 completed cardiac cycles was obtained. The transducer was placed so that the UtA blood flow was at 90° to the transducer. The vessel diameter (D) was measured perpendicular to the lumen of the vessel between the outer walls of the lumen that was delineated by the color Doppler pixels. The color gain was reduced until vessel bleed was eliminated. The transducer was then adjusted so that the direction of the UtA blood flow was parallel, and at the most within 35° of the transducer. The gate was increased to encompass all of the vessel. The waveform over the completed cardiac cycles was then selected and a computer-generated time-average mean velocity (TAMx, m/sec) and a peak velocity (Vmax) were then produced from these cycles. The UtA blood volume flow was determined as the product of the average velocity and cross-sectional area of the artery at the point where the measurements were made according to the following formula:

$$UtA\ VOL = TAMx \times \pi \times (D)/2^2 \times 60\ ml/min$$

A computer-generated pulsatility index (PI) and resistance index (RI) were also recorded in triplicate from each of the UtAs. The umbilical artery (UmA) was also examined using Doppler velocimetry in a free loop of cord and the PI and RI was determined. Each uterine or umbilical artery was measured three times, and the average of the measurements was taken.

Animal Surgery

Surgery was performed under strict aseptic conditions. The ewe's abdomen was opened via a midline laparotomy incision and the uterine arteries were identified. The main vessel was occluded manually at its most proximal part and the adenovirus vector containing the VEGF-A (n=5 ewes) or VEGF-D (n=1 ewe) gene ($5 \times 10^{11}$ particles in 10 ml normal saline) was injected slowly over 1 minute via a 23 Gauge needle and syringe. Occlusion was maintained for a further 4 minutes to give a total occlusion time of 5 minutes. This was repeated on the opposite side using adenovirus vector containing the lacZ reporter gene. Throughout the experiment the operators were blinded as to which side had received the VEGF-A adenovirus vector. The rectus sheath was closed with Mersilene tape (manufacturer) and the skin sutured with 1/0 silk (manufacturer).

Dissection

The ewe was reanaeshetized as above between 4-7 days after surgery. The ewe was ventilated for 30 minutes to achieve a steady state and to match the maternal oxygen and carbon dioxide levels, pulse and respiratory rate and temperature as closely as possible to those in the previous operation. Doppler measurements were then repeated as detailed above. The UtAs and their branches were dissected free from tissue and loosely tied. While under anaesthesia ewes were euthanased using an overdose of intravenous pentobarbitone (Euthatal, Rhône Merieux, Essex UK). The UtAs and their branches were ligated and removed without stretching and place into Krebs-Henseleit buffer solution (pH 7.4) of the following composition (in mM): 115.21 NaCl, 4.7 KCl, 1.80 $CaCl_2$, 1.16 $MgSO_4$, 1.18 $KH_2PO_4$, 22.14 NaHCO3, 11.1 glucose and 0.03 $Na_2EDTA$. The arteries were cleansed of fat and adhering tissue, and they were divided into 5 sections for analysis.

Organ Bath Experiments:

The arteries from both sides were separated and cut into individual ring segments (2-3 mm in length). Each ring was suspended between two stainless-steel L-shaped pins in 25 ml organ bath containing Krebs-Henseleit buffer solution, which was equilibrated with a mixture of 95% $O_2$-5% $CO_2$ to give a pH of 7.3 to 7.4. Temperature was held at 37° C. Rings were stretched to the equivalent of 1 gr of passive tension to allow the maximal detection of active tension. After the stretch, rings are equilibrated 1 h, during which time they are washed every 15 min. At the beginning of each experiment, rings segments were depolarized with KCl (70 mM) to determine the maximal contractile capacity of the vessel. Rings were then thoroughly washed with Krebs-Henseleit buffer and allowed to equilibrate. Functional integrity of the endothelium was confirmed routinely by the presence of relaxation induced by bradykinin (BK) $10^{-6}$ M during contraction obtained with phenylephrine (PE) ($10^{-6}$ M). To study contraction, concentration-response curves to PE ($10^{-9}$ M to $10^{-5}$ M) were determined. To study the endothelium-dependent relaxation, vessels were precontracted with PE ($EC_{70}$) and cumulative relaxation curves of BK ($10^{-10}$ M to $10^{-5}$ M) were constructed.

Histology

Tissue samples were fixed in 10% formalin overnight, transferred to 70% ethanol and processed into paraffin. Sections were stained with haematoxylin and eosin for morphological assessment. β-galactosidase was detected immunohistochemically using a mouse monoclonal antibody (Promega, Southampton) followed by a standard avidin-biotin peroxidase method. VEGF was detected immunohistochemically.

LacZ Reporter Gene Expression

β-galactosidase levels in the uterine arteries and their branches and the placentomes were determined by ELISA using a commercially available assay kit (Boehringer Mannheim, Mannheim, Germany). Levels of β-galactosidase were standardised to the protein content of each sample, determined by the bicinchoninic acid protein assay system (Pierce, Ill.). Alternatively tissues were fixed in 100% ethanol overnight then washed with PBS. Histochemical localisation of β-galactosidase expression was detected by overnight incubation of the tissues with 5-bromo-4-chloro-3-indolyl-β-D-galactoside (X-gal) in the dark. The specimens were dehydrated in 100% methanol and transferred to a benzyl benzoate and benzyl alcohol mixture (2:1 v/v). After tissue clearing the specimens were photographed under a dissection microscope using a digital camera (Olympus).

Statistical Analysis

Data was analysed using Student's t-test where appropriate. Two-way ANOVA a General Linear Model function and Tukey pairwise comparisons was performed using Minitab number and (manufacturer) for UABF blood flow analysis. All values are expressed either as means±S.E.M or means±SD. For organ bath experiments contractile effects were expressed as a percentage of the response to KCl (70 mM). Relaxation was expressed as a percentage of inhibition of phenylephrine-induced contraction. The concentrations of agonist producing half-maximum effect ($EC_{50}$ values) were expressed as $pD_2$ ($-\log EC_{50}$). The $pD_2$ values were compared by an unpaired t-test and two-way ANOVA. n values are presented as the number of donors. Statistical significance was accepted at P<0.05.

Results

Survival following the experimental procedure was 100% and there was no significant morbidity in the fetus or ewe noted at post mortem examination. The maternal pulse rate, respiratory rate and blood pressure were not significantly altered by injection of the adenovirus vectors.

Doppler Velocimetry of Maternal and Fetal Vessels

Delivery of adenovirus VEGF-A or lacZ increased the uterine artery blood flow on the side of injection in each animal, although the increase was much higher on the VEGF-A side. The mean increase was from 408 ml/min (±SD 273, range 159-925) to 1321 ml/min (±SD 727, range 391-2505). The p values are shown in Table 1 (below), The uterine artery blood flow also increased on the side of adenovirus lacZ injection from a mean of 561 ml/min (±SD 281, range 195-862) to a mean of 755 ml/min (±SD 193, range 461-1040). Total uterine artery blood flow increased on average by 1106 ml/min (±SD 767, range 286-2564).

Using a two-way ANOVA with a GLIM function and Tukey pairwise comparisons, the most significant difference was seen in the blood flow before and after injection of VEGF-A (p=0.005). The blood flow after VEGF-A injection was also significantly increased compared to blood flow before lacZ injection (p=0.019) but not significantly different to blood flow after lacZ injection (p=0.085). There was no significant difference in blood flow before lacZ injection when compared with before VEGF-A injection or when compared with after lacZ injection.

TABLE 1

|  | Post VEGF | Post lacZ | Pre VEGF |
|---|---|---|---|
| Pre lacZ | 0.019 | 0.902 | 0.940 |
| Pre VEGF | 0.005 | 0.600 |  |
| Post lacZ | 0.085 |  |  |

Injection of VEGF-D in one ewe did not increase the uterine artery blood flow (VEGF-D injected side: 1059 ml/min±SD 105 before injection to 1017 ml/min±SD 76 after; lacZ injected side 702 ml/min±SD 20 before to 724 ml/min±SD 74 after).

The blood flow in the umbilical artery was also investigated using Doppler velocimetry. There were no significant changes in the PI, RI or fetal heart rate before and after injection of VEGF-A or -D.

Organ Bath Results

Phenylephrine produced concentration-dependent contractions which were of less magnitude in arteries transduced with Ad.VEGF-A compared with Ad.lacZ transduced vessels ($E_{max}$ 148±SEM 10.9 vs 228.2±SEM 27.5, respectively; n=6 for both groups; P<0.05). Bradykinin ($10^{-11}$ to $10^{-6}$ mol/L) caused endothelium-dependent relaxation. This relaxation was significantly increased in arteries transduced with Ad.VEGF-A compared with those transduced with Ad.lacZ ($pD_2(-\log EC50)$ values were 9.11±0.01 vs 8.65±0.11, respectively; n=6 for both groups; P<0.05). 5 animals received VEGF-A, and one got VEGF-D.

VEGF Expression

VEGF protein expression was detected in the UtAs of 4 animals and the placentome of 1 animal using VEGF ELISA analysis (R and D systems, MN, USA), which was confirmed with VEGF immunohistochemistry.

LacZ Expression

The uterine arteries that were injected with adenovirus lacZ vector expressed β-galactosidase. X-gal staining performed the day after tissue sampling showed positive lacZ expression in the uterine arteries of 3 animals.

Quantification by ELISA showed significant levels of β-galactosidase expression in the uterine arteries and branches of the same three animals. Samples of uterine arteries taken from two other animals were too small for analysis and this may have contributed to the negative results in these animals.

In all cases the uterine vessels that were injected with adenovirus VEGF-A or VEGF-D were analysed as a negative control and showed no LacZ expression by X gal histochemistry, immunohistochemistry or ELISA analysis.

Discussion

In this study, the effect of adenovirus-mediated local expression of VEGF on the uterine arteries in the pregnant sheep, was examined. Using Doppler ultrasound velocimetry, the blood flow in the uterine artery was examined, and was shown to increase significantly in the side that had received adenovirus VEGF vector compared with the contralateral control side that was injected with an adenovirus carrying a reporter gene.

When these uterine arteries were examined in vitro, their relaxation response to bradykinin was significantly enhanced and their contractile response to phenylephrine was significantly impaired compared to the control side. These results suggest VEGF expression is occurring in the injected uterine arteries, and this is supported by the results of the VEGF and β-galactosidase immunohistochemistry, X-gal histochemistry and β-galactosidase ELISA.

The results of this study show that blood flow to the uterine artery significantly increases if VEGF is administered. This increase in blood flow may be sufficient to achieve an increase in fetal growth and allow delivery of the baby at a birthweight and gestational age that is compatible with survival.

The invention claimed is:

1. A method for providing treatment for intra-uterine growth retardation wherein said method comprises administering to the uterine artery of a pregnant female in need of such treatment, a gene construct encoding a VEGF peptide, wherein VEGF is expressed by the uterine artery and whereby expression increases blood flow through the uterine artery.

2. The method, according to claim 1, wherein the VEGF peptide is VEGF-A.

3. The method, according to claim 1, wherein the VEGF peptide is VEGF-D.

* * * * *